(12) United States Patent
Lui et al.

(10) Patent No.: US 8,128,636 B2
(45) Date of Patent: Mar. 6, 2012

(54) DEVICE AND METHOD FOR REMOVING LUMENLESS LEADS

(75) Inventors: Chun Kee Lui, Monroeville, PA (US); Barry E. Norlander, Freeport, PA (US)

(73) Assignee: Cook Medical Technologies LLC, Bloomington, IN (US)

( * ) Notice: Subject to any disclaimer, the term of this patent is extended or adjusted under 35 U.S.C. 154(b) by 751 days.

(21) Appl. No.: 11/704,852

(22) Filed: Feb. 9, 2007

(65) Prior Publication Data

US 2007/0191919 A1    Aug. 16, 2007

Related U.S. Application Data

(60) Provisional application No. 60/773,140, filed on Feb. 13, 2006.

(51) Int. Cl.
*A61B 17/08*    (2006.01)

(52) U.S. Cl. ......... 606/108; 606/113; 607/116; 607/118

(58) Field of Classification Search .................. 607/116, 607/119; 606/1, 108, 113
See application file for complete search history.

(56) References Cited

U.S. PATENT DOCUMENTS

| | | |
|---|---|---|
| 3,118,159 A | 1/1964 | Kollmann |
| 3,128,652 A | 4/1964 | Schinske |
| 3,243,755 A | 3/1966 | Johnston |
| 3,516,412 A | 6/1970 | Ackerman |
| 3,757,375 A | 9/1973 | Strom |
| 3,841,308 A | 10/1974 | Tate |
| 3,906,938 A | 9/1975 | Fleischhacker |
| 4,000,745 A | 1/1977 | Goldberg |
| 4,011,869 A | 3/1977 | Seiler, Jr. |
| 4,040,413 A | 8/1977 | Ohshiro |
| 4,306,562 A | 12/1981 | Osborne |
| 4,466,690 A | 8/1984 | Osypka |
| 4,471,777 A | 9/1984 | McCorkle, Jr. |
| 4,493,329 A | 1/1985 | Crawford et al. |
| 4,498,482 A | 2/1985 | Williams |
| 4,541,681 A | 9/1985 | Dorman et al. |
| 4,574,800 A | 3/1986 | Peers-Trevarton |
| 4,576,162 A | 3/1986 | McCorkle |
| 4,581,025 A | 4/1986 | Timmermans |
| 4,582,056 A | 4/1986 | McCorkle, Jr. |
| 4,621,636 A | 11/1986 | Fogarty |
| 4,706,671 A | 11/1987 | Weinrib |

(Continued)

FOREIGN PATENT DOCUMENTS

EP    0 385 920 A2    9/1990

*Primary Examiner* — Carl H Layno
*Assistant Examiner* — Pamela M Bays
(74) *Attorney, Agent, or Firm* — Brinks Hofer Gilson & Lione

(57) ABSTRACT

A device for removing from a patient a previously implanted elongated structure, such as a cardiac lead. The device includes a gripping member having a receiving portion and a capturing portion. The receiving portion defines an eyelet for receiving a length of the elongated structure. The capturing portion is movable relative to at least the eyelet of the receiving portion, and is dimensioned such that upon relative movement, the receiving portion is constrictable around a length of the elongated structure length. The receiving portion may comprise a wire and the capturing portion may comprise a collar, wherein at least a portion of the collar is movable over the eyelet to constrict the wire around the length of the elongated structure length received in the eyelet.

15 Claims, 5 Drawing Sheets

U.S. PATENT DOCUMENTS

| | | | | |
|---|---|---|---|---|
| 4,732,154 | A | 3/1988 | Shiber | |
| 4,762,128 | A | 8/1988 | Rosenbluth | |
| 4,762,130 | A | 8/1988 | Fogarty et al. | |
| 4,773,432 | A | 9/1988 | Rydell | |
| 4,791,939 | A | 12/1988 | Maillard | |
| 4,796,642 | A | 1/1989 | Harris | |
| 4,834,090 | A | 5/1989 | Moore | |
| 4,848,342 | A | 7/1989 | Kaltenbach | |
| 4,886,496 | A | 12/1989 | Conoscenti et al. | |
| 4,886,500 | A | 12/1989 | Lazarus | |
| 4,943,289 | A | 7/1990 | Goode et al. | |
| 4,988,347 | A | 1/1991 | Goode et al. | |
| 5,011,482 | A | 4/1991 | Goode et al. | |
| 5,013,310 | A | 5/1991 | Goode et al. | |
| 5,061,257 | A | 10/1991 | Martinez et al. | |
| 5,066,285 | A | 11/1991 | Hillstead | |
| 5,066,772 | A | 11/1991 | Tang et al. | |
| 5,067,489 | A | 11/1991 | Lind | |
| 5,098,374 | A | 3/1992 | Othel-Jacobsen et al. | |
| 5,098,440 | A * | 3/1992 | Hillstead | 606/108 |
| 5,106,368 | A | 4/1992 | Uldall et al. | |
| 5,108,368 | A | 4/1992 | Hammerslag et al. | |
| 5,112,299 | A | 5/1992 | Pascaloff | |
| 5,171,222 | A | 12/1992 | Euteneuer et al. | |
| 5,190,528 | A | 3/1993 | Fonger et al. | |
| 5,207,683 | A | 5/1993 | Goode et al. | |
| 5,221,255 | A | 6/1993 | Mahurkar et al. | |
| 5,231,996 | A | 8/1993 | Bardy et al. | |
| 5,234,437 | A | 8/1993 | Sepetka | |
| 5,250,038 | A | 10/1993 | Melker et al. | |
| 5,329,923 | A | 7/1994 | Lundquist | |
| 5,342,371 | A | 8/1994 | Welter et al. | |
| 5,346,497 | A | 9/1994 | Simon et al. | |
| 5,387,219 | A * | 2/1995 | Rappe | 606/108 |
| 5,409,469 | A | 4/1995 | Schaerf | |
| 5,415,639 | A | 5/1995 | VandenEinde et al. | |
| 5,454,790 | A | 10/1995 | Dubrul | |
| 507,751 | A | 4/1996 | Goode et al. | |
| 5,522,819 | A * | 6/1996 | Graves et al. | 606/113 |
| 5,533,968 | A | 7/1996 | Muni et al. | |
| 5,549,615 | A | 8/1996 | Hocherl et al. | |
| 5,562,620 | A | 10/1996 | Klein et al. | |
| 5,562,678 | A * | 10/1996 | Booker | 606/113 |
| 5,618,267 | A | 4/1997 | Palestrant | |
| 5,628,754 | A | 5/1997 | Shevlin et al. | |
| 5,632,749 | A | 5/1997 | Goode et al. | |
| 5,645,533 | A | 7/1997 | Blaeser et al. | |
| 5,697,936 | A | 12/1997 | Shipko et al. | |
| 5,725,512 | A | 3/1998 | Swartz et al. | |
| 5,725,551 | A | 3/1998 | Myers et al. | |
| 5,976,107 | A | 11/1999 | Mertens et al. | |
| 6,007,517 | A | 12/1999 | Anderson | |
| 6,027,475 | A | 2/2000 | Sirhan et al. | |
| 6,033,402 | A | 3/2000 | Tu et al. | |
| 6,136,005 | A | 10/2000 | Goode et al. | 606/108 |
| 6,167,315 | A | 12/2000 | Coe et al. | |
| 6,190,349 | B1 | 2/2001 | Ash et al. | |
| 6,190,353 | B1 | 2/2001 | Makower et al. | |
| 6,264,671 | B1 | 7/2001 | Stack et al. | |
| 6,315,781 | B1 | 11/2001 | Reinhardt et al. | |
| 6,324,434 | B2 | 11/2001 | Coe et al. | |
| 6,350,271 | B1 | 2/2002 | Kurz et al. | |
| 6,358,256 | B1 | 3/2002 | Reinhardt | |
| 6,361,541 | B1 | 3/2002 | Barnhart | |
| 6,379,319 | B1 | 4/2002 | Garibotto et al. | |
| 6,394,978 | B1 | 5/2002 | Boyle et al. | |
| 6,409,863 | B1 | 6/2002 | Williams et al. | |
| 6,419,674 | B1 | 7/2002 | Bowser et al. | |
| 6,544,270 | B1 | 4/2003 | Zhang | |
| 6,562,049 | B1 | 5/2003 | Norlander et al. | |
| 6,695,858 | B1 | 2/2004 | Dubrul et al. | |
| 2002/0077686 | A1 | 6/2002 | Westlund et al. | |

* cited by examiner

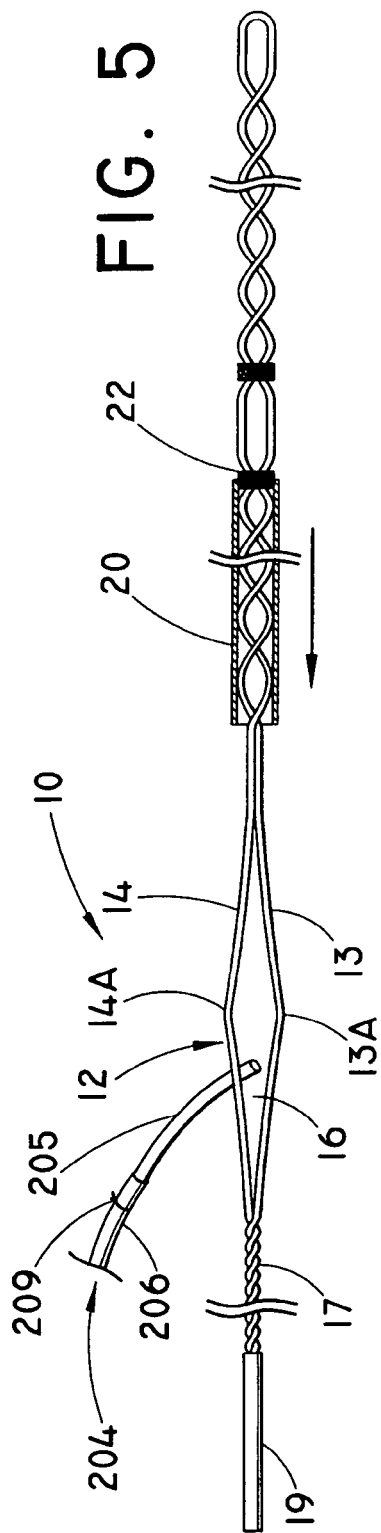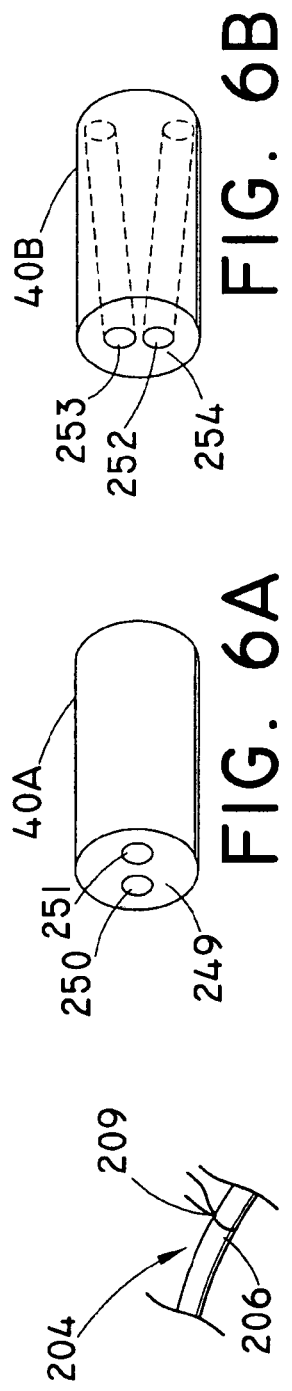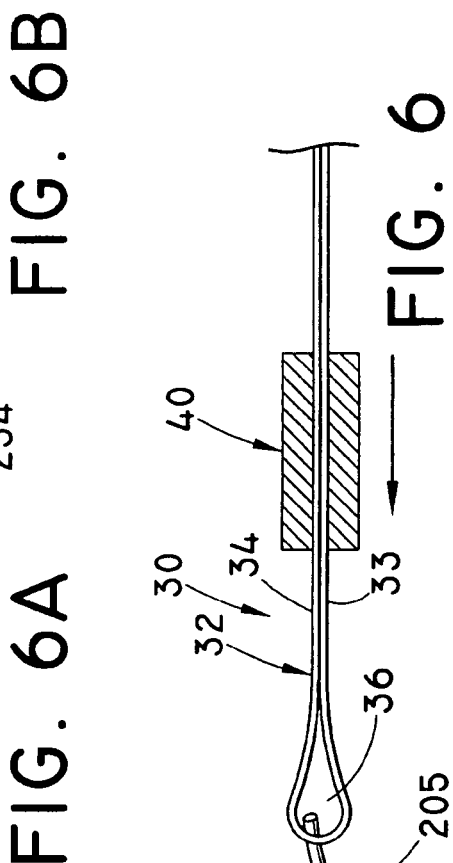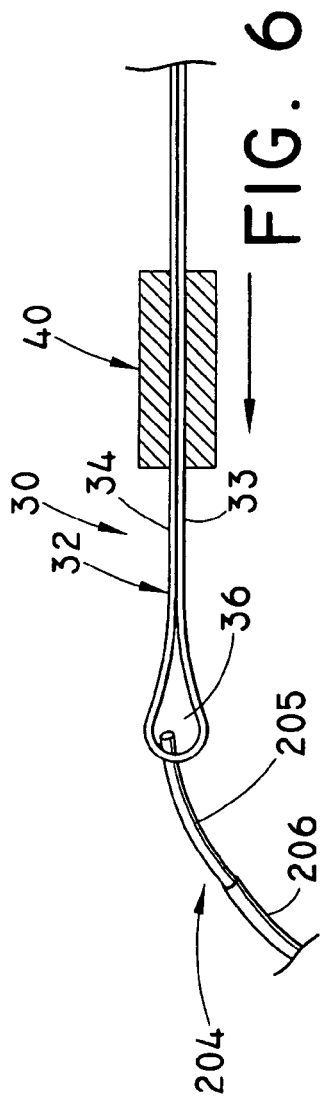

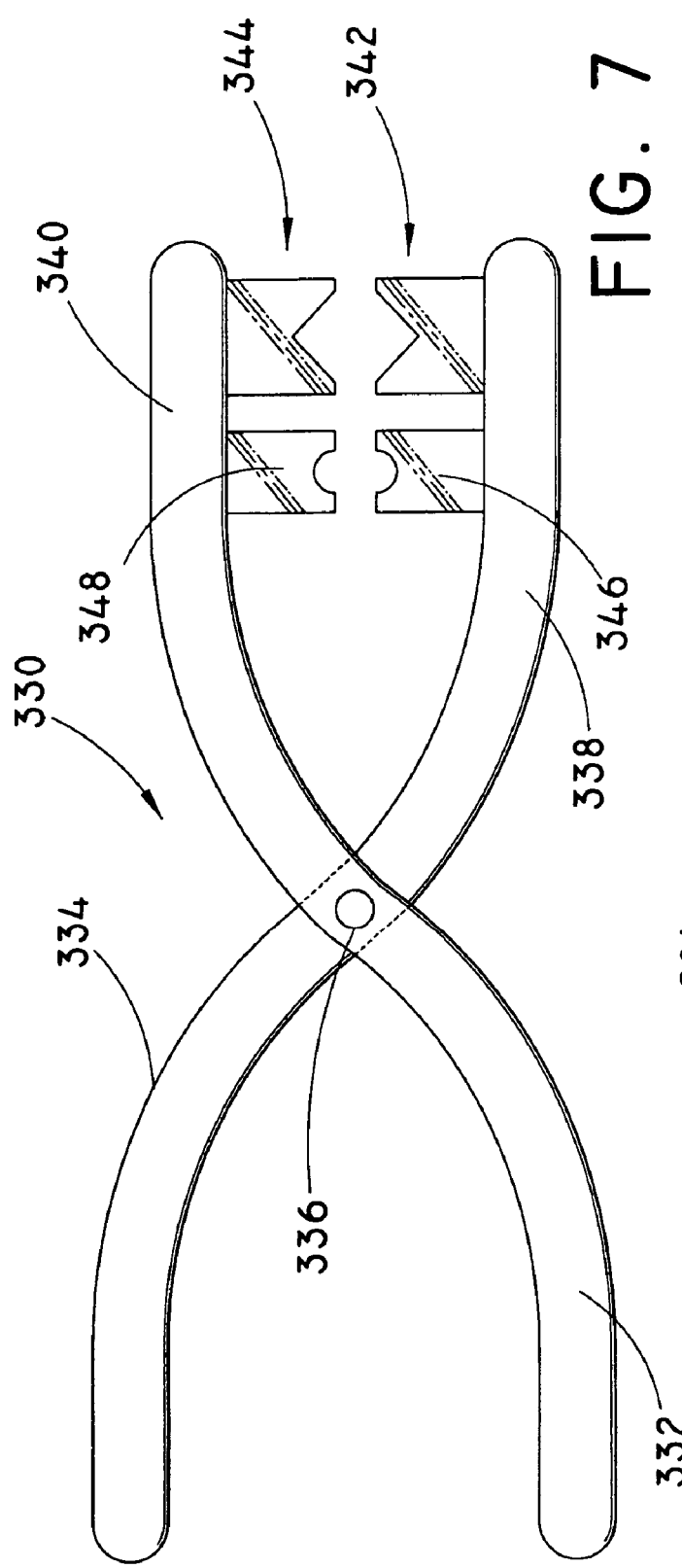
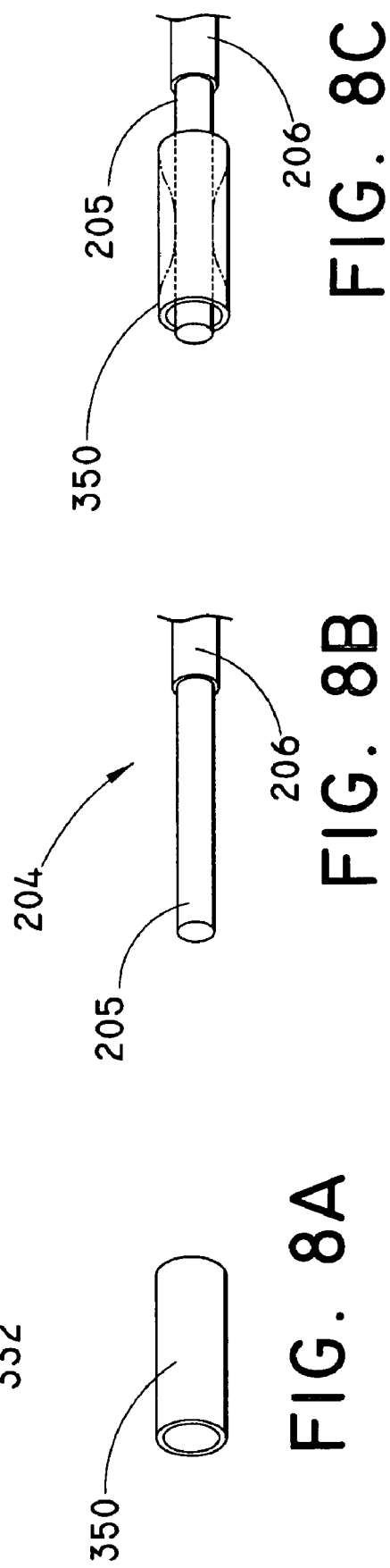

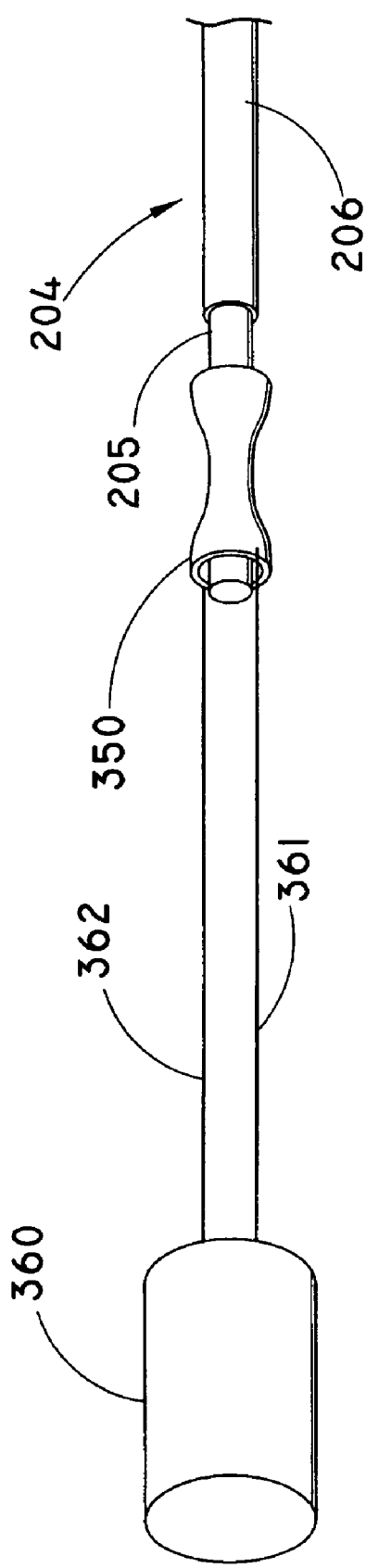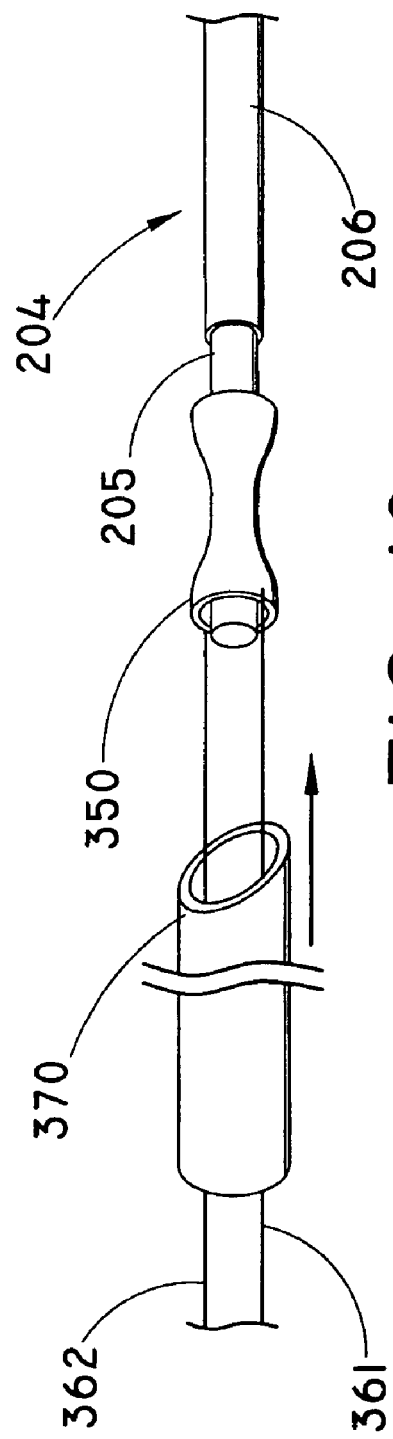

DEVICE AND METHOD FOR REMOVING LUMENLESS LEADS

RELATED APPLICATION

The present patent document claims the benefit of the filing date under 35 U.S.C. §119(e) of Provisional U.S. Patent Application Ser. No. 60/773,140, filed Feb. 13, 2006, which is hereby incorporated by reference.

BACKGROUND

1. Technical Field

This invention relates generally to a device and method for removing an implanted elongated structure from a patient, and more particularly, to a device and method for removing an implanted cardiac lead from a patient.

2. Background Information

A variety of medical treatments and surgical methods entail implanting an elongated structure in the body of a human or veterinary patient. Examples of such elongated structures include catheters, sheaths and cardiac electrical leads (such as pacemaker leads and defibrillator leads), and a variety of other devices. Over time, it can become necessary or desirable to remove the implanted elongated structure from the body of the patient. However, problems can be encountered in attempting removal of an elongated structure implanted in biological tissue.

For example, a heart pacemaker is typically implanted in a subcutaneous tissue pocket in the chest wall of a patient, and a pacemaker lead is positioned in the vascular system of the patient, extending from the pacemaker and through a vein into a chamber of the patient's heart. The pacemaker lead commonly includes a coiled structure such as an electrical wire coil for conducting electrical signals (such as stimulating and/or sensing signals) between the pacemaker and the heart. Defibrillator leads are generally similar and, like pacemaker leads, are located about the heart, but are affixed both internally and externally of the heart. Some leads include one or more coaxial or lateral helical wire coils having a hollow inner passageway, or lumen, that extends the entire length of the wire coil or coils. Other leads, generally referred to as "lumenless" leads, may be made with a cable or a tightly wound coil without a hollow inner passageway. In either case, the cable or wire coils are surrounded by an electrically insulating material such as a flexible tube, sheath or coating. The insulating material, generally formed of silicone or polyurethane, serves simultaneously to protect the cable and wire coils from body fluids, and in the case of bi-polar leads, to insulate the wire coils from one another.

While cardiac electrical leads typically have a useful life of many years, over time pacemaker and defibrillator leads may become encapsulated by fibrotic tissue against the heart itself or the wall of the vein, or against other surrounding tissue. Encapsulation is especially encountered in areas where the velocity of the flow of blood is low. The fibrotic tissue is tough and makes it difficult to remove the lead from the area of the heart without causing trauma to the area. For example, when small diameter veins through which a pacemaker lead passes become occluded with fibrotic tissue, separating the lead from the vein can cause severe damage, such as dissection or perforation of the vein. Furthermore, separation of the lead from the vein is usually not possible without restricting or constraining movement of the lead, i.e., fixing the lead in position with respect to the patient, and in particular, with respect to the patient's vein.

To avoid this and other possible complications, some useless pacemaker or other leads are simply left in the patient when the pacemaker or defibrillator is removed or replaced. However, such a practice can incur the risk of an undetected lead thrombosis, which can result in stroke, heart attack, or pulmonary embolism. Such a practice can also impair heart function, as the presence of plural leads can restrict the heart valves through which the leads pass.

There are many other reasons why removal of a useless lead is desirable. For example, if there are too many leads positioned in a vein, the vein can be obliterated. Multiple leads can be incompatible with one another, interfering with the pacing or defibrillating function. An inoperative lead can migrate during introduction of an adjacent second lead, and mechanically induce ventricular arrhythmia. Other potentially life-threatening complications can require the removal of the lead as well. For example, removal of an infected pacemaker lead is desirable, so as to avoid septicemia or endocarditis.

Surgical removal of a heart lead in such circumstances often involves open heart surgery, with its accompanying risks, complications and significant costs. A variety of successful methods and apparatus have been devised as alternatives to open heart surgery for heart lead removal. Several such successful methods and apparatus are described in, among others, U.S. Pat. No. 5,697,936, titled "Device for Removing an Elongated Structure Implanted in Biological Tissue," assigned to the assignee of the present application. U.S. Pat. No. 5,697,936 is a continuation-in-part of U.S. Pat. No. 5,507,751, titled "Locally Flexible Dilator Sheath," which was in turn a continuation-in-part of U.S. Pat. No. 5,632,749, titled "Apparatus for Removing an Elongated Structure Implanted in Biological Tissue," which was a divisional of U.S. Pat. No. 5,207,683, titled "Apparatus for Removing an Elongated Structure Implanted in Biological Tissue;" which was a continuation-in-part of U.S. Pat. No. 4,943,289, titled "Apparatus for Removing an Elongated Structure Implanted in Biological Tissue;" which was a continuation-in-part of U.S. Pat. No. 5,011,482, titled "Apparatus for Removing an Elongated Structure Implanted in Biological Tissue;" which was a continuation-in-part of U.S. Pat. No. 5,013,310, titled "Method and Apparatus for Removing an Implanted Pacemaker Lead;" which was a continuation-in-part of U.S. Pat. No. 4,988,347, titled "Method and Apparatus for Separating a Coiled Structure from Biological Tissue." All of the aforementioned patents describe methods and/or apparatus for removing an implanted elongated structure, and are incorporated by reference as if fully set forth herein.

Although the devices and methods described in the incorporated-by-reference patents have proven to be effective for removing elongated structures implanted in biological tissue, there is a continuing desire for improved devices for such purposes. Desirably, such improved devices will have a more compact profile than existing devices, be effective for the removal of implantable structures having a lumen as well as lumenless devices, and be structured to minimize trauma to the patient.

BRIEF SUMMARY

The present invention addresses the shortcomings of the prior art. In one form thereof, the invention comprises a device for removing from a patient a previously implanted elongated structure, such as an implanted cardiac lead. The device includes a gripping member having a receiving portion and a capturing portion. The receiving portion defines an eyelet for receiving a length of the elongated structure. The capturing portion is movable relative to at least the eyelet of the receiving portion, and is dimensioned such that upon this relative movement, the receiving portion is constrictable around the length of the elongated structure. In a preferred embodiment, the receiving portion comprises a wire and the capturing portion comprises a collar, such that at least a portion of the collar is movable over the eyelet to constrict the wire around the length of the elongated structure length received in the eyelet.

In another form thereof, the invention comprises a kit for use in removing a previously implanted elongated structure from a patient. The kit includes a gripping member comprising a collar and a wire. The collar has at least one passageway therethrough. The wire extends through the passageway, and is configured to define an opening for receiving a length of the elongated structure. The passageway is dimensioned such that upon movement of the collar, the wire is constrictable around the elongated structure length. The kit may also include a cutter for cutting an outer insulating layer from the implantable elongated structure.

In yet another form thereof, the invention comprises a method for removing from a patient a previously implanted elongated structure having an inner core, and an outer layer covering at least a portion of the inner core. The method includes the steps of exposing a segment of the inner core; providing a gripping member for gripping the exposed inner core segment, the gripping member comprising a wire and a collar slidable over at least a portion of the wire and in closely spaced relationship therewith, the wire defining an eyelet for receiving the exposed segment, the collar sized and movable relative to the wire such that an outer dimension of the eyelet is constrictable around the segment of the elongated member for capturing the segment therein; threading a portion of the exposed segment through the eyelet; constricting the eyelet by axially sliding the collar along the wire toward the eyelet, such that the exposed segment of the elongated member is captured therein; and removing the elongated member from the patient.

In still another form thereof, the invention comprises a method for removing from a patient a previously implanted elongated structure, wherein the elongated structure has an inner core and an outer layer covering at least a portion of the inner core. The method includes the steps of exposing a segment of the inner core; providing a gripping member for gripping the exposed segment, the gripping member comprising a sleeve dimensioned to be slidable over at least a portion of the exposed segment; crimping at least a portion of the sleeve onto the exposed core segment; and removing the elongated member from the patient by withdrawing the sleeve.

BRIEF DESCRIPTION OF THE DRAWINGS

FIG. 5 illustrates one embodiment of a gripping device according to the present invention, partially in section, shown pulling an implanted structure;

FIG. 5A illustrates a knot drawn back to allow complementary tension to the insulation;

FIG. 6 illustrates another embodiment of a gripping device;

FIGS. 6A and 6B illustrate alternative embodiments of a collar portion of the gripping device;

FIG. 7 illustrates another embodiment of a cutter apparatus that may be used to prepare a lead targeted for removal;

FIGS. 8A to 8C illustrate the use of a sleeve member for removing an implantable structure;

FIG. 9 is a variation of the embodiment of FIGS. 8A-8C, wherein the sleeve is provided with an extension handle; and FIG. 10 shows the embodiment of FIG. 9, and also illustrates a dilator sheath for removing fibrotic tissue from the implanted structure.

DETAILED DESCRIPTION OF THE DRAWINGS AND THE PRESENTLY PREFERRED EMBODIMENTS

Figure 1:
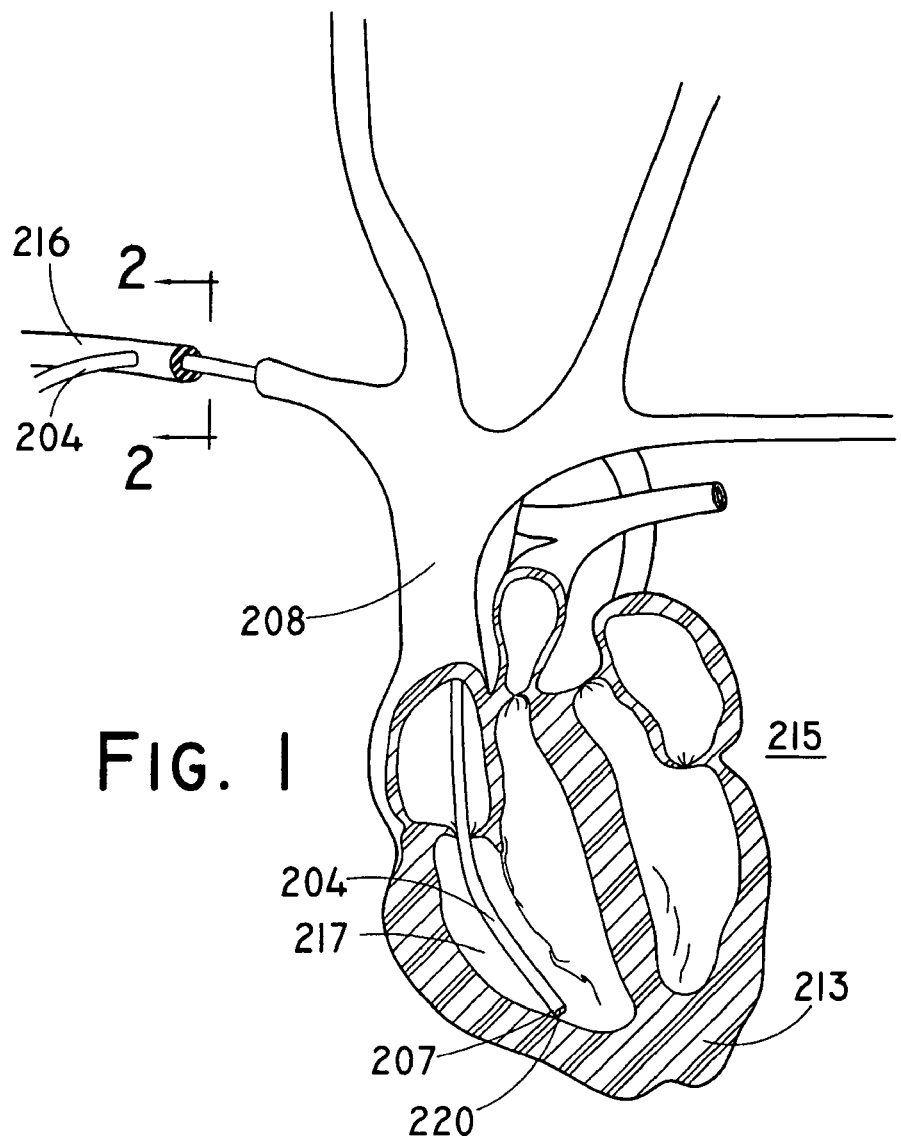
FIG. 1 is a partial cross-sectional view of a heart having an electrical pacemaker lead implanted therein.

For the purposes of promoting an understanding of the principles of the invention, reference will now be made to the embodiments illustrated in the drawings, and specific language will be used to describe the same. It should nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

In the following discussion, the terms "proximal" and "distal" will be used to describe the opposing axial ends of the device described, as well as the axial ends of various component features. The term "proximal" is used in its conventional sense to refer to the end of the device (or component thereof) that is closest to the operator during use of the device. The term "distal" is used in its conventional sense to refer to the end of the device (or component thereof) that is initially inserted into the patient, or that is closest to the patient.

In one form thereof, the present invention comprises a device for grasping and providing traction to an implanted elongated structure targeted for removal from a body vessel, such as an artery or a vein. In one intended use, the device is used for removing a cardiac pacemaker lead. A non-limiting list of other uses includes removing other implanted elongated structures, such as defibrillator leads, other cardiac electrical leads, catheters, sheaths, cannulae and the like. In another form thereof, the present invention comprises a method for removing an implanted elongated structure.

When the implanted elongated structure targeted for removal is a cardiac pacemaker lead, the distal end of the structure will be located within the vascular system of the patient, and in particular, within a chamber of the patient's heart (such as in an atrium or ventricle of the heart). When the implanted elongated structure is a defibrillator lead, the distal end of the structure will be located either in or about the heart of the patient. The distal ends of other types of implanted elongated structures targeted for removal may not be and need not be near the heart.

For convenience, the following discussion will refer to the removal of a cardiac pacemaker lead. However it should be understood that this is no way intended to be a limitation on the scope of the invention, and that at least the other elongated structures referred to above may also be removed by the inventive device and method.

Typically, a cardiac pacemaker lead comprises an inner core, comprising a cable or a coil, surrounded by a layer of insulating material. As explained previously, some pacemaker leads have a lumen extending therethrough, while others ("lumenless" leads) do not. The inventive device is useful for pulling implanted leads having a lumen, as well as lumenless leads. The device is believed to have particular utility in removing lumenless leads, since there are many other removal devices presently available that may be used to remove leads having a lumen.

When the inventive device and method is to be used for removal of a pacemaker or a defibrillator lead, those skilled in the art will appreciate that the lead should initially be severed from the connector prior to any attempts to remove the lead. The connector has a much larger diameter than the remainder of the lead, and only an unreasonably large dilator sheath could fit over the connector.

A known technique for removing an implanted pacemaker lead involves advancing a two-part dilator sheath over the lead to break up fibrous adhesions that have grown between the interior of the vessel wall and the implanted device, and that are preventing easy withdrawal of the implanted device. However, if the implanted device is bowed or cantilevered in any manner within the vessel, the dilator sheath cannot be readily advanced over the device. The structure of the inventive lead-pulling device allows for tensional forces to be applied longitudinally along the length of the lead body. This limits the bowing or cantilevering of the lead, such that a dilator sheath may be readily passed over the lead puller/lead interface without obstruction.

The invention may be better understood with reference to the drawings. Depicted in FIG. 1 is a partial cross-sectional view of the heart 215 of a patient. Heart 215 is connected to a plurality of arteries and veins, such as the right subclavian vein 216 through which an electrical heart pacemaker lead 204 has been implanted. The lead passes through the superior vena cava 208 and into the right ventricle 217 of the heart. The distal end of the lead includes an electrode 220 for electrically stimulating the heart. The electrode is secured to the apex of the right ventricle with a plurality of tines 207, which in time, become securely attached to the ventricle wall by endothelial tissue forming around the heart lead tip. Some ventricles are relatively smooth on the inside, but most have trabeculae amongst which the tines are secured into position.

Figure 2:
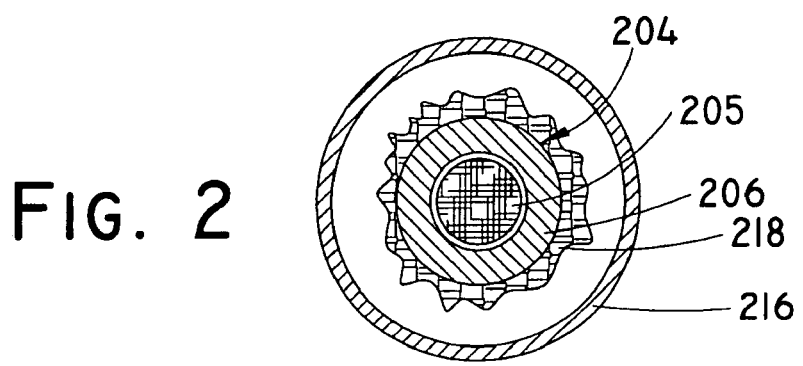
FIG. 2 is a sectional view of a portion of the right subclavian vein illustrated in FIG. 1, showing the electrical lead passing therethrough.

A sectional view of pacing lead 204 in right subclavian vein 216 is shown in FIG. 2. In this view, pacing lead 204 is encapsulated in fibrotic tissue 218. Pacing lead 204 is shown as a lumenless lead. Those skilled in the art will appreciate that the inventive device is also useful with other types of leads. Non-limiting examples of other types of lead with which the inventive device may be used include leads having a lumen, as well as leads fabricated from a "coiled" inner wire (conductor). In the embodiment shown, lead 204 comprises an interior braided cable 205 which mechanically and electrically connects the proximal connector to the electrode. The cable is covered by a layer of insulating material 206. Insulating material 206 typically comprises a hollow tube that surrounds the cable, and prevents fluid from making contact with the cable. Insulating material 206 is formed of a relatively flexible material well-known for such use, such as silicone or polyurethane.

A gripping mechanism (as described hereinafter) is provided for engaging the pacemaker lead cable so that the lead can be removed from the body vessel. The gripping mechanism has a compact profile, which allows the physician to use the smallest possible diameter dilator sheath for loosening the lead from the surrounding fibrotic tissue. By utilizing a gripping mechanism having a compact profile in combination with a small diameter dilator sheath, the trauma to the patient resulting from the insertion of the sheath and gripping mechanism can be minimized. In addition, the gripping mechanism can be utilized to remove an implantable structure from a smaller diameter vessel when compared to a gripping device having a larger profile.

In order to allow use of a compact profile gripping mechanism, the mechanism is structured such that it grips an exposed portion of the cable from which the insulating layer has previously been removed. Since the pacemaker lead typically comprises a hard interior cable portion and a softer outer insulating layer, it is desirable to utilize a cutter that cuts only through the insulating layer and not through the cable, so that the insulating layer can be removed from the underlying cable.

Figure 3:
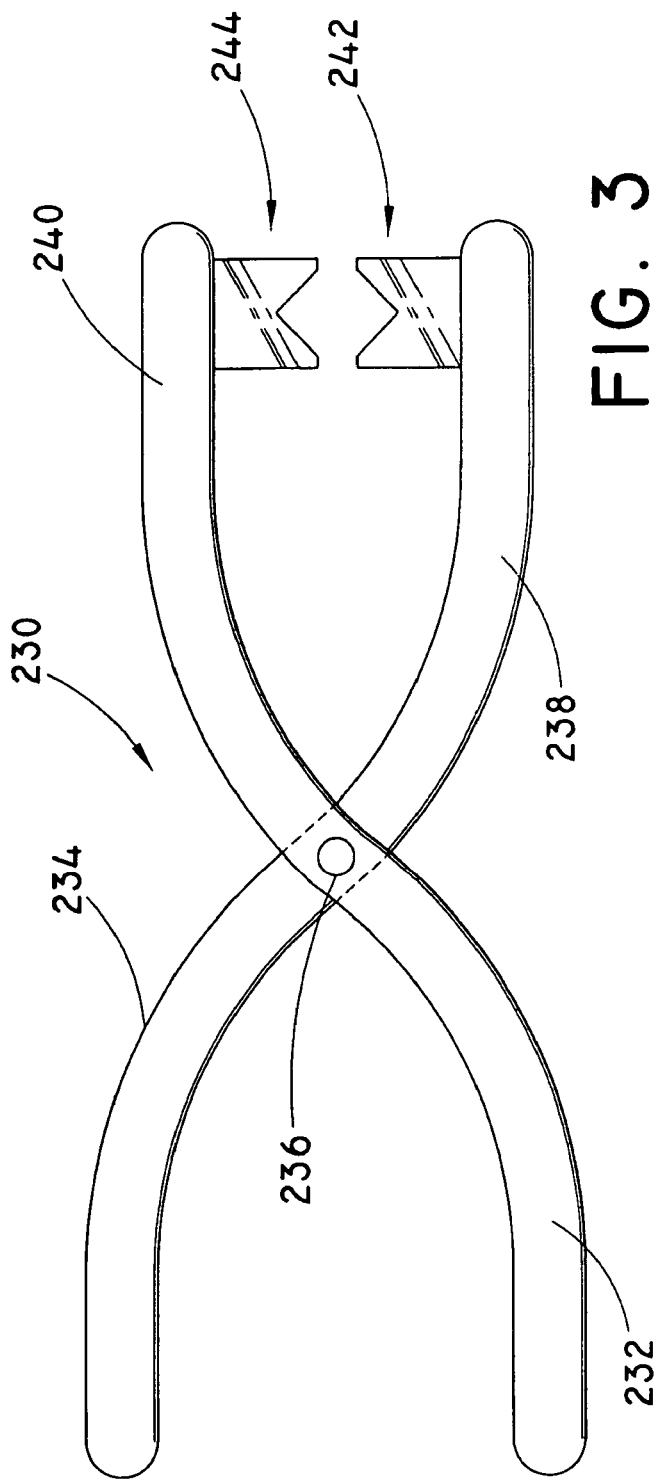
FIG. 3 is a side view of a cutter apparatus that may be utilized to prepare a pacemaker lead for removal.
Figure 4:
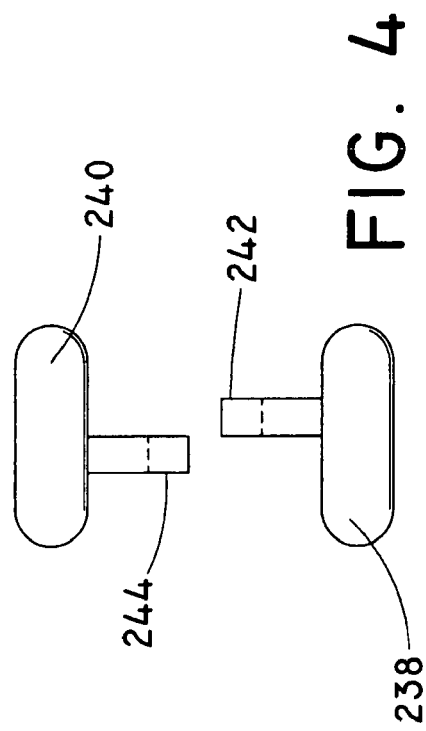
FIG. 4 is a front view of the cutter apparatus of FIG. 3.

FIG. 3 illustrates a side view and FIG. 4 illustrates a front view of one example of a soft-tipped cutter 230 suitable for such use. Soft-tipped cutter 230 is structured for cutting soft material in proximity to harder material, and to avoid or minimize damage to harder material which one does not intend to cut. During removal of the pacing lead, a portion of the soft insulating material 206 is therefore initially removed to expose the interior cable 205. Soft-tipped cutter 230 includes grasping handles 232, 234 that are pivotable around a hinged connection 236, for selectively opening and closing arms 238, 240. Cutting jaws 242, 244 are provided at the distal end of respective arms 238, 240. Jaws 242, 244 are preferably V-shaped, as shown in FIG. 3.

It is preferable that jaws 242, 244 are formed of a material that is softer than that of the conductor portion of the electrical cable lead, but is harder than the insulating material. This arrangement allows cutter 230 to cut through the insulating layer 206, but not through the conductor cable 205. Non-limiting examples of suitable materials for the jaws include aluminum, fiber glass, epoxy, and the like.

The jaws are preferably arranged on arms 238, 240 in an offset manner as best shown in the front view of FIG. 4. When handles 232, 234 are grasped and squeezed together, arms 238, 240 are urged together in conventional fashion. However, due to the composition of jaws 242, 244, as well as their offset arrangement, the jaws cut through the insulating material when they are urged together, but do not cut into the conductor cable. As a result, the cut portion of the insulating material may simply be peeled away in the proximal direction from the cut line to expose the underlying cable. Preferably, the lead is cut such that at least a couple of inches of insulation can be removed from the exposed proximal end of the lead. Removal of the insulating material allows the use of a more compact gripping mechanism than could be used if the insulating material was left in place.

In addition to the cutter described, other cutter configurations may be employed. For example, a punch type (e.g. side) cutter may be utilized. In addition, if desired, the cutter handles and the jaws may be formed of the same composition, as long as care is taken to insure that the cutter cuts only through the insulating material, and not through the interior cable. As another alternative, the cutter handles and jaws may be formed of the same material, and then the jaws may be subjected to a softening treatment. For example, the entire cutter device may be formed of a metal or alloy, such as stainless steel 440C, and the jaws could be locally softened using conventional means, e.g., a laser beam.

Although the jaws (cutter tips) are shown in FIGS. 3 and 4 as being mounted on scissors-type handles, other arrangements may be substituted. For example, the jaws may be provided on a vise-like tool, or mounted on a laparoscopic device. Similarly, the jaws need not each have the same configuration. For example, one of the jaws may be shaped like a wedge, with the opposing jaw having a flat surface. The jaws may also be of different hardnesses. In some embodiments, the cutter need not even be provided with discrete jaws. For example, the handles of a pair of scissors, where the handles overlap, may be locally softened to function as soft tips, or the handles may be made of soft materials. As still another alternative, soft inserts may be placed on otherwise hard cutting surfaces.

A preferred embodiment of a gripping device 10 according to the present invention is shown in FIG. 5. Gripping device 10 includes a receiving portion, such as wire 12, and a suitable capturing device, such as collar 20. Preferably, wire 12 comprises an elongated wire structure folded back upon itself to comprise adjacent wire lengths 13, 14. At the terminal end 17 of wire 12, wire lengths 13, 14 may be engaged by well-known means, such as by twisting, soldering, welding, and/or adhesion, to define en eyelet 16. In the embodiment shown, solder 19 is applied to the terminal end of wire 12 at wire lengths 13, 14.

One or more knots, or suture-ties, 209 are preferably tied on the lead near the location where the insulation has been cut. A sufficient number of knots may be tied such that the knot(s) will not pull into the insulation, but the number should not be so large as to cause difficulty when sliding a dilator sheath over the lead. FIG. 5A illustrates a knot drawn back to allow complementary tension to the insulation. This arrangement may be used to limit the longitudinal compression of a lead insulating sheath caused by the advancing of the dilator sheath, which may otherwise result in snaking of the insulating sheath, and in undesirable friction or binding against the dilator sheath.

Preferably, wire 12 is formed from stainless steel round wire, nickel-chromium round wire, or a nickel-titanium superelastic wire, and has a diameter of about 0.017 inch (0.43 mm) Those skilled in the art will appreciate that wires of other compositions, cross-sectional geometries, and diameters may be substituted, as long as the wire has sufficient strength to withstand the pulling forces. Collar 20 is preferably fabricated from stainless steel or other metals or metal alloys by machining or by forming from a tube. Alternatively, collar 20 may be formed from plastics or composite materials; however in this event it is advantageous to utilize stiff or filled plastics or composites in order to maintain the compactness of the sleeve.

The inside diameter of collar 20 is sized such that the respective wire high points 13A, 14A that define the eyelet are squeezed together as collar 20 is advanced in the distal direction toward the eyelet. This causes wire lengths 13, 14 to bite on the entrapped cable end, thereby holding the cable end within the eyelet and preventing disengagement. Thus, for example, with a wire 12 having a diameter of about 0.017 inch (0.43 mm), and an inside diameter of collar 20 of about 0.04 inch (1.0 mm), a lead cable 205 of 0.012 inch (0.30 mm) diameter may be threaded through the eyelet. In this case, when collar 20 is advanced over wire 12 and cable end 205, an interference of about 0.006 inch (0.15 mm) results, thereby effectively compressing, or locking, the cable inside the eyelet. This interference enhances the efficacy of the device in maintaining wire capture, and helps prevent the collar from sliding in a backward direction.

The diameter of optional reduced diameter collar portion 22 is sized to prevent collar portion 22 from sliding over the eyelet 16 when cable end 205 is positioned in the eyelet, or alternatively, to permit collar portion 22 to slide over the eyelet only upon the application of a large amount of force to the collar. This feature prevents unintended over-advancing of the collar beyond the eyelet.

In the example described, reduced diameter portion 22 has an opening of about 0.035 inch (0.89 mm). This allows free sliding of collar 20 along wire portion 12 until reduced diameter portion 22 reaches the entrapped lead. This provides the physician with a tactile feel as to when to stop advancing the collar. Typically, the size of the eyelet is about 0.1 inch (2.5 mm) wide and 0.8 inch (20 mm) long. With these dimensions, the eyelet is sufficiently large to facilitate threading of cable 205 through the eyelet.

Typically, a minimum of about 2 inches (5.08 cm) of outer insulating layer 206 of pacemaker lead 204 is cut and peeled away in the manner described above. Once the segment of insulating layer has been removed, a leading end of exposed cable 205 is threaded through eyelet 16, as shown in FIG. 5. Collar 20 is then urged in the direction of the arrow in FIG. 5 to compress the opposing wire portions 13, 14 that define eyelet 16 around the cable as previously described. Preferably, collar 20 has a length of about 1 inch (2.54 cm), and an outer diameter not exceeding about 6 French (0.079 inch; 2 mm). Typically, the outer diameter may be about 0.06 inch (1.5 mm). Those skilled in the art will appreciate that these dimensions are exemplary only, and that larger, or smaller dimensions may be substituted in an appropriate case. Alternatively, collar 20 may comprise a sheath several inches long or greater, with a single inside diameter throughout all or a substantial portion of the entire length. This increased length would facilitate containment of excess cable inside the sheath, and allow extension of the sheath over the proximal end of the lead insulation. Because of its length, it is preferred that the sheath be flexible in bending. For example, it may be fabricated from a plastic tubing, with optional braiding or coil for increased circumferential strength. Reduced collar portion 22 may also be omitted in this design.

Following locking of the exposed end of the cable between wire portions 13, 14 of the eyelet, a conventional dilator sheath may be slid over the lead puller and advanced into the patient to sever the fibrotic sheaths that have grown around the implanted pacemaker lead. The lead may then pulled from the vessel by withdrawing it in the proximal direction through the dilator sheath. Due to the compact profile of the gripping device 10, a smaller diameter dilator sheath may be utilized when compared to the use of a gripping device not having this profile, thereby minimizing trauma to the patient.

Another embodiment of a gripping device 30 is shown in FIG. 6. In this embodiment gripping device 30 includes a wire 32 and a collar 40 as before. Adjacent wire lengths 33, 34, are aligned to define a terminal loop, which comprises eyelet 36. The terminal portion of wire 32 is not twisted or otherwise engaged in the manner of gripping device 10. Those skilled in the art will appreciate that although this embodiment is satisfactory for many diameters of cable 205, wire 32 and/or collar 40, it may not provide the type of wedging action that is obtained in the embodiment of FIG. 5 when the collar is advanced in the direction of the arrow. Accordingly, with some diameters of cable, wire and collar, the lead may not be as securely locked when compared to the gripping ability of the device of FIG. 5. However, even though the embodiment of FIG. 5 may provide better gripping of the cable end, gripping may add an element of stress to the cable. This may reduce its tensile pull strength somewhat when compared to the embodiment of FIG. 6.

In another alternate embodiment, the collar may be provided with more than one lumen, as illustrated in FIGS. 6A and 6B. FIG. 6A illustrates a collar 40A having dual parallel lumens 250, 251. FIG. 6B also illustrates a collar 40B having dual lumens 252, 253. In FIG. 6B, lumens 252, 253 are angled or wedged such that the lumens are spaced a greater distance at the proximal end of the collar and a smaller distance at the distal end. With these embodiments, one end of a wire is threaded through each of the lumens such that a loop extends distal to the collar, as shown in the embodiment of FIG. 6. Cable end 205 is threaded through the loop as before, and the wire ends may be pulled in the proximal direction such that the cable end is captured and held by the wire against distal face 249, 254 of respective collars 40A and 40B.

FIG. 7 illustrates another type of soft-tipped cutter 330 that may be used to prepare an exposed end of the lead targeted for removal. Soft-tipped cutter 330 may include handles 332, 334, hinge 336, arms 338, 340 and jaws 342, 344. The features are generally similar to the corresponding features of cutter 230 as illustrated in FIGS. 3 and 4. However, unlike cutter 230, cutter 330 is also provided with a second set of jaws, in this case, crimping jaws 346, 348.

Soft-tipped cutter 330 may be advantageously used with an alternative embodiment of a gripping device illustrated in FIGS. 8A-8C. In this embodiment, the proximal end of a pacemaker lead 204 is initially cut, and insulation 206 is removed to expose a portion of the cable 205 as before. A sleeve 350 is then provided over the cut and bared portion of the cable. FIG. 8A illustrates the sleeve 350, and FIG. 8B illustrates the cut and bared cable 204. Preferably, sleeve 350 has a generally cylindrical profile with an inner diameter that exceeds the outer diameter of cable 205 by only a nominal amount, such that sleeve 350 is insertable over cable 205 as illustrated in FIG. 8C.

In this embodiment, jaws 346, 348 of cutter 330 comprise a crimping mechanism that may be used to crimp sleeve 350 onto cable portion 205. The broken lines of FIG. 8C illustrate the crimped profile of the sleeve. Use of a crimped sleeve eliminates any necessity to place a knot at the proximal end of the lead, and prevents lead extension devices from sliding proximally off the lead or other device targeted for removal.

The sleeve 350 can in theory have any diameter, but the preferred dimension is one that has an outer diameter after engagement of less than 0.092 inch (2.4 mm; 7 French). In this manner, the sleeve can be drawn through a dilation sheath having an inner diameter of 7 French. Sleeve 350 can have a consistent wall thickness across in longitudinal length, or it may have a varied wall thickness to allow for adequate sleeve distortion that may be required to form a locking engagement. Alternately, a crimping pattern may include multiple sleeve distortions following multiple vectors.

A variation of the embodiment of FIGS. 8A-8C is shown in FIG. 9. In this embodiment, crimped sleeve 350 is provided with an extension handle 360 that extends in the proximal direction. The extension handle can include one or more elongated wires that are attachable to and extend in the proximal direction from the sleeve. In the embodiment illustrated in FIG. 9, extension handle 360 comprises two elongated wires 361, 362 that are attachable to and extend from sleeve 350. The extension handle can be used to apply direct traction to the targeted lead, and as a guide for passage of a conventional dilator sheath. FIG. 10 illustrates the use of dilator sheath 370 in combination with sleeve 350 and extension wires 361, 362. The direction of movement of dilator sheath 370 in the vessel to cut fibrotic tissue is shown by the arrow in the figure.

The gripping device has been described herein for use with conventional pacemaker leads having a single cable or coil surrounded by the insulating material. However, the principles of the present invention are also applicable to removal of a bi-polar lead, such as a bi-polar pacing lead. In bi-polar leads, an additional conductor coil surrounds the cable, with an insulating material between the conductor coil and the cable. In this instance, the insulating material between the inner cable and the coil is also cut and removed. For best results, the coil is stretched out and as much insulation as possible is removed.

The present invention has been described as a gripping device, and as methods for removing an elongated structure from a patient using various embodiments of the inventive gripping device. In addition to the foregoing, the invention also includes a kit for use in removing a previously implanted elongated structure from a patient.

It is therefore intended that the foregoing detailed description be regarded as illustrative rather than limiting, and that it be understood that it is the following claims, including all equivalents, that are intended to define the spirit and scope of this invention.

What is claimed is:

1. A device for removing from a patient a previously implanted elongated structure, the device comprising:
a gripping member, said gripping member comprising a pair of generally adjacent wire lengths, and a collar having a passageway extending therealong, each of said generally adjacent wire lengths received in said collar passageway and positioned such that a segment of each wire length extends distally from the passageway, said segments aligned to define an eyelet therebetween, said eyelet configured and arranged for receiving a length of said implanted elongated structure therein, wherein both of said wire length segments are simultaneously movable relative to said collar such that upon said relative movement said eyelet constricts around said implanted elongated structure length.

2. The device of claim 1, wherein at least a portion of said collar is movable over said eyelet for constricting said eyelet around said elongated structure length.

3. The device of claim 1, wherein said wire lengths have respective distal end portions, said distal end portions being engaged by at least one of twisting, soldering, welding, and adhering.

4. The device of claim 1, wherein said collar has an outer diameter not exceeding about 2 mm (0.079 inch).

5. The device of claim 1, wherein said collar has two lumens aligned generally side-by-side along a length of said collar, one of said wire lengths extending through each of said lumens.

6. The device of claim 1, wherein said pair of generally adjacent wire lengths comprise an elongated wire structure folded back upon itself.

7. The device of claim 1, wherein each of said segments is configured to comprise a high point along said wire length, said high points defining said eyelet.

8. The device of claim 1, wherein said adjacent wire lengths comprise a terminal loop, said terminal loop defining said eyelet.

9. The device of claim 1, wherein said collar comprises an inside diameter sized to receive said constricted eyelet and said implanted elongated structure length.

10. The device of claim 9, wherein said inside diameter of said collar comprises a reduced diameter proximal end portion.

11. The device of claim 1, wherein each wire length segment has a terminal end, and wherein said terminal end of a first wire segment is fixedly engaged with a terminal end of a second wire segment.

12. The device of claim 11, wherein said terminal ends are engaged by at least one of twisting, soldering, and welding.

13. A device for removing from a patient a previously implanted elongated structure, the device comprising:

a gripping member, said gripping member comprising a pair of generally adjacent wire lengths, and a collar having a passageway extending therealong, each of said generally adjacent wire lengths received in said collar passageway and positioned such that a segment of each wire length extends distally from the passageway, each said segment having a terminal distal end, said respective terminal ends engaged to one another by one of twisting, soldering, and welding, said segments aligned upon said engagement to define an eyelet therebetween, said eyelet configured and arranged for receiving a length of said implanted elongated structure therein, said collar movable relative to said wire length segments and dimensioned relative to said eyelet such that upon said movement said eyelet constricts around said implanted elongated structure length.

14. The device of claim 13, wherein said respective terminal ends are engaged to define a wire tip, said wire tip including solder applied thereto.

15. The device of claim 13, wherein said collar has two lumens aligned generally side-by-side along a length of said collar, one of said wire lengths extending through each of said lumens.

* * * * *

UNITED STATES PATENT AND TRADEMARK OFFICE
CERTIFICATE OF CORRECTION

PATENT NO. : 8,128,636 B2  Page 1 of 1
APPLICATION NO. : 11/704852
DATED : March 6, 2012
INVENTOR(S) : Chun Kee Lui et al.

It is certified that error appears in the above-identified patent and that said Letters Patent is hereby corrected as shown below:

On the Title Page

Under References Cited - U.S. Patent Documents, please delete cited reference "507,751" and insert in lieu thereof --5,507,751--.

Signed and Sealed this
Seventeenth Day of April, 2012

David J. Kappos
*Director of the United States Patent and Trademark Office*